(12) United States Patent
Feng et al.

(10) Patent No.: US 9,945,830 B2
(45) Date of Patent: Apr. 17, 2018

(54) STANDARD SOLUTION WITH CLEANING REAGENT FOR WET CHEMISTRY ANALYZER

(71) Applicant: Rosemount Analytical Inc., Irvine, CA (US)

(72) Inventors: Chang-Dong Feng, Long Beach, CA (US); Hoang Minh Nguyen, Highland, CA (US)

(73) Assignee: Rosemount Inc., Shakopee, MN (US)

( * ) Notice: Subject to any disclaimer, the term of this patent is extended or adjusted under 35 U.S.C. 154(b) by 0 days.

(21) Appl. No.: 15/003,042

(22) Filed: Jan. 21, 2016

(65) Prior Publication Data

US 2017/0212091 A1 Jul. 27, 2017

(51) Int. Cl.
*G01N 33/18* (2006.01)

(52) U.S. Cl.
CPC .................................. *G01N 33/18* (2013.01)

(58) Field of Classification Search
None
See application file for complete search history.

(56) References Cited

U.S. PATENT DOCUMENTS

| | | |
|---|---|---|
| 3,773,423 A | 11/1973 | Hach |
| 4,131,428 A | 12/1978 | Diggens |
| 4,251,218 A | 2/1981 | Diggens |
| 4,263,104 A | 4/1981 | Diggens et al. |
| 4,865,992 A | 9/1989 | Hach et al. |
| 5,230,863 A | 7/1993 | Salpeter |
| 5,300,442 A | 4/1994 | Frant |
| 6,306,284 B1 | 10/2001 | Yang et al. |
| 7,381,564 B2 | 6/2008 | Matschenko et al. |
| 7,842,510 B2 | 11/2010 | Shimizu et al. |
| 2005/0196319 A1 | 9/2005 | Bogren et al. |
| 2011/0027893 A1* | 2/2011 | Kathe ................ G01N 33/1806 436/62 |
| 2013/0122597 A1 | 5/2013 | Xiao et al. |
| 2015/0099303 A1 | 4/2015 | Butcher et al. |

FOREIGN PATENT DOCUMENTS

WO WO2009144331 A1 12/2009

OTHER PUBLICATIONS

"Model CFA-3000—Colorimetric Valve-Pump-based Monitor", Instruction Manual, Sep. 2014, Emerson Process Management. (78 pages).
Second Chinese Office Action for Chinese Patent Application No. 201620383857.0 dated Nov. 21, 2016, 2 pages. With English translation.
International Search Report and Written Opinion for International Patent Application No. PCT/US2017/012153, dated Apr. 20, 2017, 13 pages.

* cited by examiner

*Primary Examiner* — Xiaoyun R Xu
(74) *Attorney, Agent, or Firm* — Christopher R. Christenson; Kelly, Holt & Christenson, PLLC

(57) ABSTRACT

A calibration solution for a wet chemistry analyzer is provided. The solution comprises a calibration agent. The solution also comprises a cleaning agent. The cleaning agent is selected such that the wet chemistry analyzer is simultaneously cleaned and calibrated.

10 Claims, 5 Drawing Sheets

STANDARD SOLUTION WITH CLEANING REAGENT FOR WET CHEMISTRY ANALYZER

BACKGROUND

Chemistry analyzers are used in a variety of industries to provide indications of process variables within a process stream. Indications can be provided locally by an analyzer and/or remotely to one or more suitable devices. Indications may be helpful to provide control and/or monitoring of a chemical process.

One particular type of chemistry analyzer is an on-line silica analyzer. An on-line silica analyzer is configured to generate a reaction in a process sample in order to render silica detectable. Such analyzers are useful in detecting a silica concentration in boiler water, boiler feed water, demineralized water, or steam condensate, for example. While such analyzers are useful in a variety of industries, they are of particular use in power plant boilers. In such systems, silica can form silicate deposits that can damage turbines and other equipment used in the water steam turbine cycle. Accordingly, power plants with high pressure turbines generally monitor silica concentrations carefully in order to ensure effective detection and removal or remediation. However, while the present discussion focuses on the example of silica analyzers, the methods and embodiments described herein may be applicable to analyzers drawn to measuring concentrations of other chemicals.

The discussion above is merely to provide for general background information, and is not intended to be used as an aide in determining the scope of the claimed subject matter.

SUMMARY

A calibration solution for a wet chemistry analyzer is provided. The solution comprises a calibration agent. The solution also comprises a cleaning agent. The cleaning agent is selected such that the wet chemistry analyzer is simultaneously cleaned and calibrated.

DETAILED DESCRIPTION OF ILLUSTRATIVE EMBODIMENTS

Figure 1A:
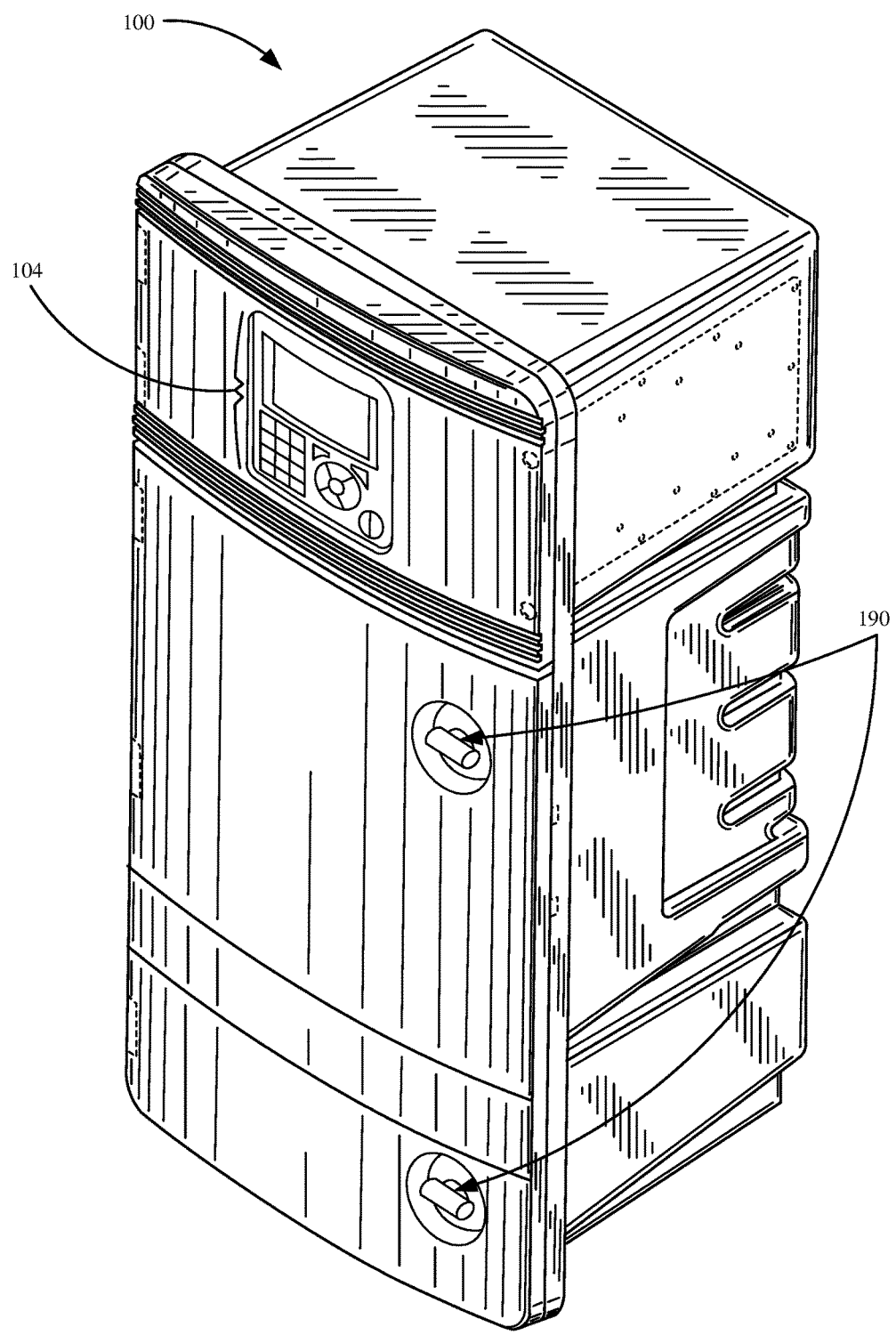
FIGS. 1A and 1B illustrate exemplary external and internal views of a wet chemistry analyzer in accordance with one embodiment of the present invention.

Colorimetric detection methods are available to measure concentration of reactants, products or trace compounds of a reaction, for example by measuring absorbance or transmissivity of a reaction mixture during a reaction process. However, colorimetric detection works better when the compound to be measured has a readily detectable absorbance or transmissivity. For some compounds, an analyzer must allow the compound to undergo a reaction to make it readily detectable. For example, measuring silica in a process stream often utilizes the molybdenum blue method to render the silica easily detectable.

In one embodiment, a chemical reaction begins with one or more reactants that are, during a reaction period, converted at least partially to one or more products. Additionally, under some conditions, the reactants may be converted to one or more unwanted byproducts. A reaction is considered complete at the end of a reaction time. Some reactions progress to completion, given enough time, such that all reactant molecules are converted to product molecules. Other reactions only progress until an equilibrium is achieved, such that there will always be some reactant molecules and some product molecules in a reaction mixture. In such reactions, the point at which an equilibrium is achieved may also be considered a completion point.

Many reactions have a known reaction rate such that it can be predicted, based on the reaction rate, when the reaction will reach completion. However, many factors such as adequate mixing, temperature, pressure, concentration of initial reactant, or the present of sufficient catalysts may affect the reaction rate and cause a reaction to proceed faster, or slower, than expected. Therefore, it may be helpful, in one embodiment, for an analyzer to be configured to detect a completed reaction. As used herein, reactant solution refers to substantially unreacted solution provided at the beginning of a reaction. As used herein, a reaction mixture may refer to a mixture within a reaction chamber at any point during the reaction period. As used herein, a product solution refers to the mixture after completion is achieved.

One problem present in the use of on-line wet chemistry analyzers, is the build-up of silica, or other unwanted deposits, for example within process piping and reaction or detection chambers. Build-up of deposits, for example silica deposits, can affect measurements of the on-line wet chemistry analyzer, as well as its function. For example, during regular operation, the inner surfaces of tubing and chambers responsible for sample transfer, conducting heteropoly blue reactions, and conducting colorimetric detection, can become coated with precipitants from the reaction, or other impurities from the sample. As the deposits accumulate, the performance of the analyzer will be compromised. Additionally, internal deposits may result in inaccurate sensor readings by the analyzer, or alter the anticipated reaction rate, resulting in a faster or slower reaction time than expected.

One potential solution to get rid of deposit buildup within the machinery of an analyzer is to periodically run a cycle of the analyzer using a cleaning solution. The frequency of cleaning cycles may be based on, for example, detected build-up or recommended by a manufacturer. However, a separate cleaning cycle requires that a wet chemistry analyzer be configured to store, or otherwise have access to, the cleaning solution on a regular basis. Often, this equates to the analyzer storing the cleaning solution in a reagent storage compartment. A separate cleaning cycle also requires the analyzer to conduct additional process cycles so that the cleaning solution can be applied to the internal mechanisms of the machine. These additional cycles cause further wear on the analyzer, and render the analyzer unavailable for sample analysis. A solution is desired for removing silica, or other deposits, from the wet chemistry analyzer during a separate cleaning solution and cleaning cycle.

An on-line silica analyzer will generally employ a known reaction process to render silica readily detectable by colorimetric analysis. One example of such a reaction is the molybdenum blue method. In the molybdenum blue method, molybdate (usually in the form of potassium molybdate) reacts with silica in a process sample or solution and generates, as a product of the reaction, silicomolybdic acid, a compound readily detectable by colorimetric detection. In accordance with the molybdenum blue method, a silica concentration in water is measured based on a detected color of silicomolybdic acid. The concentration of silica can be calculated using a detected transmissivity of silicomolybdic acid and the Beer-Lambert Law (Equation 1 below). The Beer-Lambert Law states that there is a logarithmic dependence between the transmission (or transmissivity), T, of light through a substance and the product of the absorption coefficients of the substance, a, and the distance that the light travels through the material (i.e., path length), L. The Beer-Lambert Law is expressed as follows.

$$T = \frac{I}{I_o} = 10^{-aL} = 10^{-\epsilon Lc} \qquad \text{Equation 1}$$

The absorption coefficient can be written as a product of the molar absorptivity (extinction coefficient) of the absorber, E, and the molar concentration, c, of the absorbing species in the material where I and $I_o$ are the intensity of the incident light and the transmitted light, respectively.

A wet chemistry analyzer, from time to time, requires calibration in order to ensure accurate measurements throughout its lifecycle. Calibration may comprise running a cycle of the analyzer using calibration fluid with a known absorbance/transmissivity, instead of reactants or other reagent fluids.

Figure 1B:
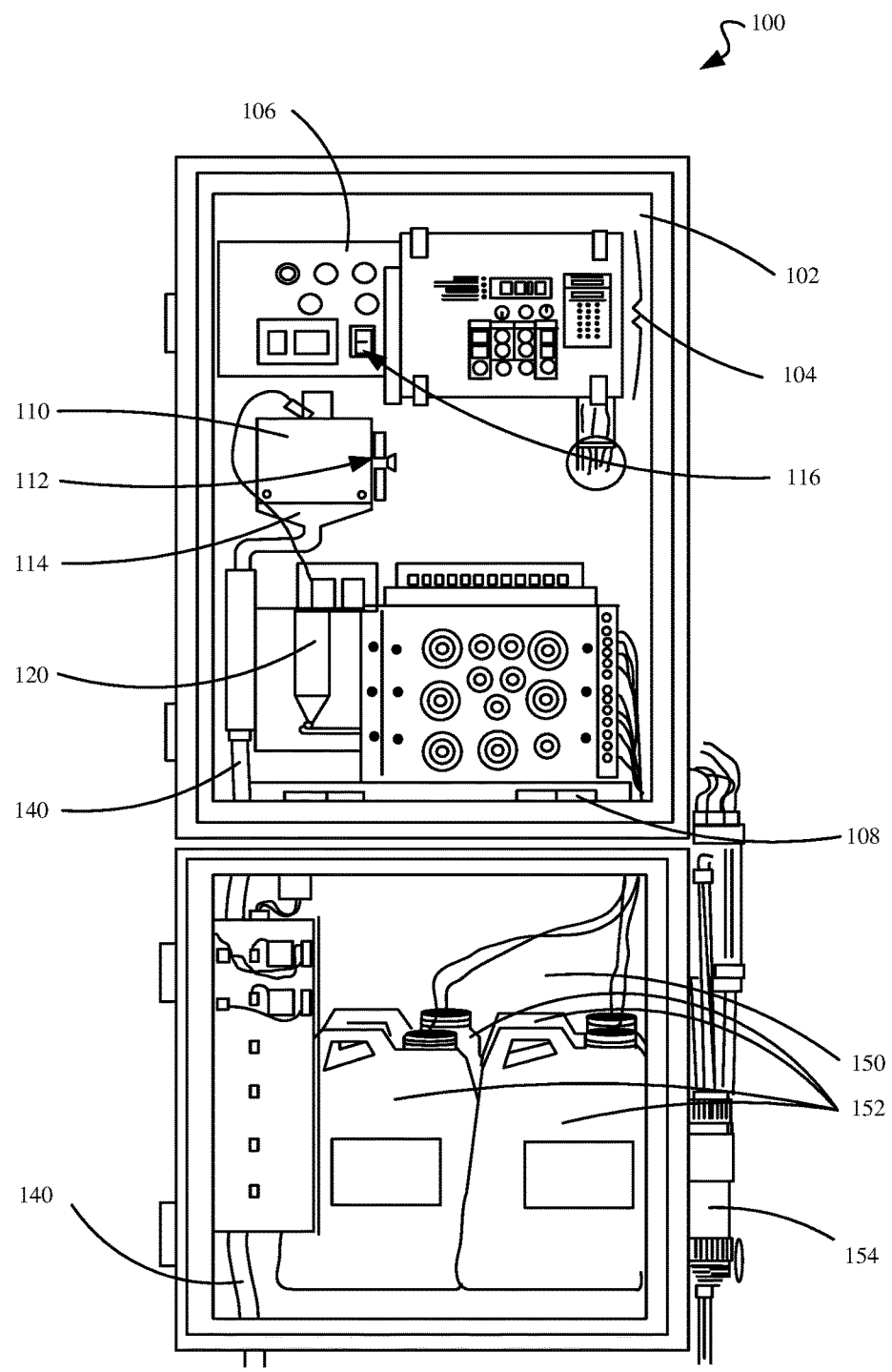

FIGS. 1A and 1B illustrate exemplary external and internal views of a wet chemistry analyzer in accordance with one embodiment of the present invention. Analyzer 100, as shown in FIG. 1A, is one example of a wet chemistry analyzer. However, other designs and configurations of wet chemistry analyzers are also envisioned. Analyzer 100 may have one or more input or output mechanisms, such as display 104, such that an operator can engage with analyzer 100. For example, in one embodiment, display 104 may comprise a set of input keys such that an operator can set parameters for, initiate or terminate, an analysis cycle. In another embodiment, display 104 may be configured to report concentration, or other process variable indications, regarding a process fluid within analyzer 100. Wet chemistry analyzer 100 may also have an opening mechanism 190, for example a door with a handle as shown in FIG. 1A, that allows an operator to access the internal components of analyzer 100.

FIG. 1B illustrates an exemplary internal view of a wet chemistry analyzer 100 in accordance with one embodiment of the present invention. The internal components of the wet chemistry analyzer 100, may be accessible, in one embodiment, by actuating handle 190, shown in FIG. 1A.

Wet chemistry analyzer 100 may comprise, in one embodiment, a main cabinet 102, and a reagent cabinet 150. However, in at least one embodiment, reagents are stored in the same cabinet as some or all of the circuitry of wet chemistry analyzer 100. In one embodiment, in main cabinet 102, for example, an operator may be able to access and interact with display 104. In one embodiment, display 104 may present currently detected process variables within wet chemistry analyzer 100. Additionally, in one embodiment, by engaging display 104, an operator may be able to engage different cycle profiles of wet chemistry analyzer 100, for example conducting a reaction, calibrating the machine, or initiating a separate cleaning cycle. In one embodiment, some or all of the reactions within a wet chemistry analyzer may require use of a power supply 106, and may be controlled by an on/off switch 116.

As a wet chemistry analyzer primarily handles fluids, in one embodiment, a leak detector 108 may be located within one or both of main cabinet 102 and reagent cabinet 150 such that a leak within a process streams is readily detectable. Such a leak may be reported, in one embodiment, using display 104.

In one embodiment, wet chemistry analyzer 100 is responsible for conducting colorimetric analysis to detect, for example, a concentration of silica within a process sample. Colorimetric assembly 110, may be configured to analyze a product mixture, for example, resulting from exposing a process stream to potassium molybdate, in order to make silica readily detectable. Colorimetric assembly 110 may comprise a colorimetric locking assembly 112, which, in one embodiment, is fluidically coupled to a waste drain pan 114 which may be connected to a waste tube 140. The reaction of silica with potassium molybdate may take place, in one embodiment, in reaction cell 120. The contents of reaction cell 120 are provided to colorimetric assembly 110, which detects a silica concentration within the process stream.

Reagent cabinet 150 may house one or more process fluids 152. Process fluids 152 may comprise any of reactants, solvents, air streams, catalysts, calibration solutions, and/or other fluid. Some or all of the housed fluids 152 may, in one embodiment, be fluidically coupled such that fluid 152 can travel from reagent cabinet 150 to main cabinet 102, for example, using one or more valve pump assemblies configured to provide the reagents, as needed, to reaction cell 102, and/or colorimetric assembly 110. In one embodiment, wet chemistry analyzer 100 also comprises an overflow sampling assembly 154 configured to receive overflow materials from any of the chambers of wet chemistry analyzer 100 and provide them to a waste stream 140.

Figure 2:
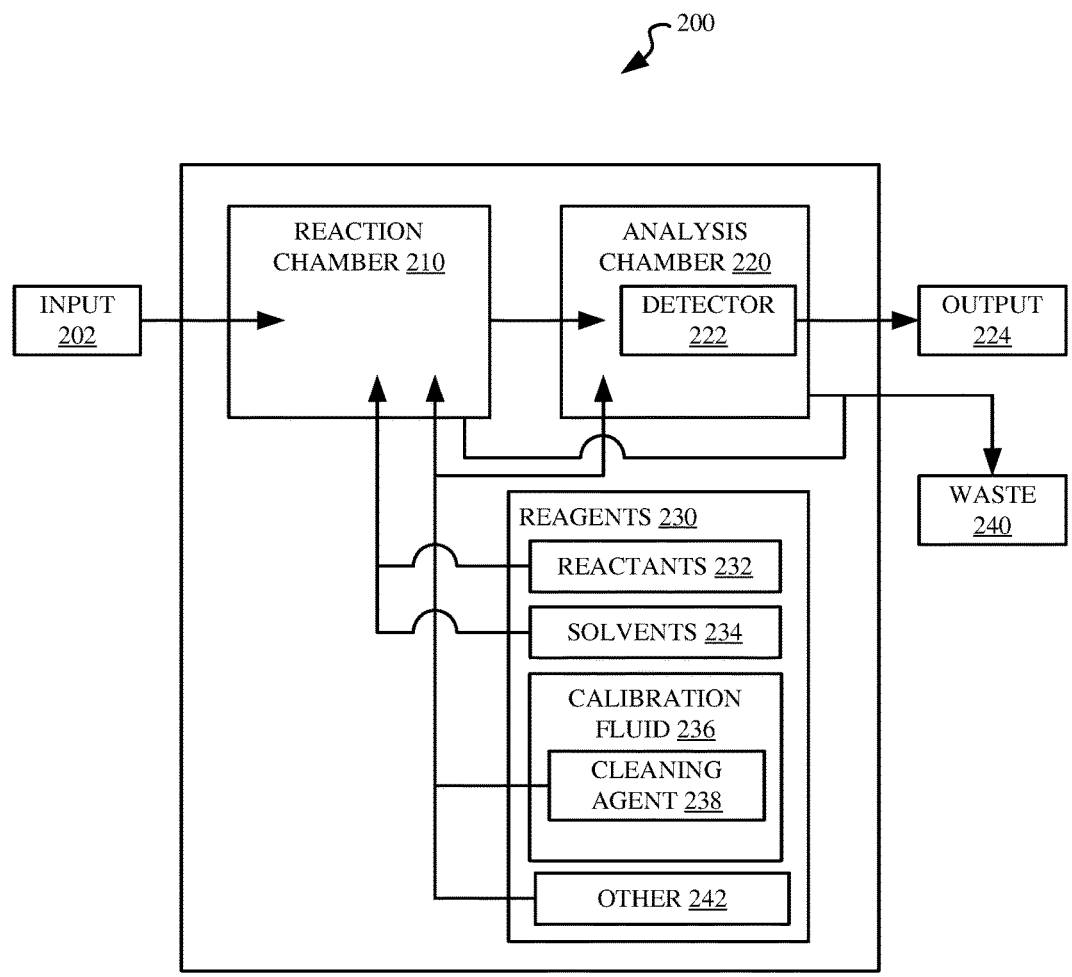
FIG. 2 illustrates a simplified block diagram of a wet chemistry analyzer in accordance with one embodiment of the present invention.

FIG. 2 illustrates a simplified block diagram of a wet chemistry analyzer in accordance with one embodiment of the present invention. As illustrated in FIG. 2, in one embodiment, a wet chemistry analyzer 200 comprises a reaction chamber 210 and an analysis chamber 220. However, in another embodiment, analysis is done on a reaction mixture within reaction chamber 210 such that a separate analysis chamber 220 is not necessary. In one embodiment, reaction chamber 210 is configured to conduct a molybdenum blue reaction to render silica within a process stream more readily detectable.

Reaction chamber 210 receives reagents from store 230, which may comprise, in one embodiment, any of reactants 232, solvents 234, calibration fluid 236 or other fluid 242. In one embodiment, other fluid 242 comprises a mixing agent, for example compressed air, or a catalyst for a reaction to be conducted within wet chemistry analyzer 200. In one embodiment, reaction chamber 210 comprises an input mechanism 202. For example, input 202 may comprise a user interface configured to receive a command from an operator, for example, to conduct an analysis, calibration, or cleaning cycle. Once the analysis chamber 220 has completed an analysis, and detector 222 has output the desired information to output 224, in one embodiment, any remaining sample is provided to a waste stream 240.

In one embodiment, once a reaction reaches completion, samples of the product mixture are provided to an analysis chamber 220. Analysis chamber 220 comprises a detector 222 configured to analyze the provided sample, and detect a concentration of silica within the sample. Detector 222 measures transmissivity and/or absorbance of silica within the sample and calculates a corresponding concentration using the Beer-Lambert Law discussed above.

A detected concentration may be designated as a process output 224, and provided to an operator in any one of a number of suitable formats. For example, in one embodiment absorbance is reported. In another embodiment, concentration is reported. In another embodiment, another desired measurement is reported. The desired process variable may be reported, for example, on an external display associated with an analyzer 200. In another embodiment, the desired process variable is wirelessly transmitted to a separate mobile operator device.

Periodically, analyzer 200 may require cleaning, for example to remove silica or other deposits that have built up within any of the process streams or reaction chambers. In one embodiment, cleaning is accomplished by providing a cleaning agent 238 within a calibration fluid 236. This may allow, for example, simultaneous cleaning and calibration of wet chemistry analyzer 200, eliminating the need for a separate cleaning cycle. Another advantage of a calibration fluid 236 containing cleaning agent 238 is the need for fewer tanks within reagent housing 230, as well as corresponding pumps, valves and other components associated with a cleaning cycle. This may even allow for a smaller wet chemistry analyzer 200. Additionally, eliminating a separate cleaning cycle may extend the life expectancy of wet chemistry analyzer 200, and reduce time spent completing separate calibration and cleaning operations.

Cleaning agent 238 may be selected based on the reagents that have been used within the wet chemistry analyzer 200. For example, if acids are used within the wet chemistry analyzer 200, a strong base may be preferred in order to remove build-up of acid precipitates. However, in another embodiment, if basic materials are used within the wet chemistry analyzer 200, a strong acid may be desired. Strong acids and bases are defined, for example, as molecular compounds that ionize to completion in aqueous solution, for example into an $H^+$ (acid) or $OH^-$ (base) and a corresponding anion or cation. Some examples of strong acids that may be utilized to remove basic precipitates include HCl (Hydrogen Chloride), $HNO_3$ (Nitric Acid), $H_2SO_4$ (Hydrogen Sulfide), HBr (Hydrogen Bromide), HI (Hydrogen Iodide), $HClO_4$ (Hydrogen Chlorate) and other strong acids as defined by the Brønsted-Lowry definition and/or the Lewis theory of acids and bases. Some examples of strong bases that may be utilized to remove acidic precipitates include hydroxides, such as LiOH (Lithium Hydroxide), NaOH (Sodium Hydroxide), KOH (Potassium Hydroxide, and/or other strong bases as defined by the Brønsted-Lowry definition and/or the Lewis theory of acids and bases. Additionally, acidic or basic cleaning agents 238 may be selected based on a desired pH of the calibration solution.

In one embodiment, cleaning agent 238 comprises sodium hydroxide and is configured to remove silicomolybdic acid deposits within analyzer 200. In one embodiment, cleaning agent 238 comprises 0.1% by weight of calibration fluid 236. In one embodiment, cleaning agent 238 comprises 0.2% by weight of calibration fluid 236. Other concentrations of cleaning agent 238 are also contemplated, for example 0.05% by weight, 0.15% by weight, or 0.25% by weight.

Figure 3:
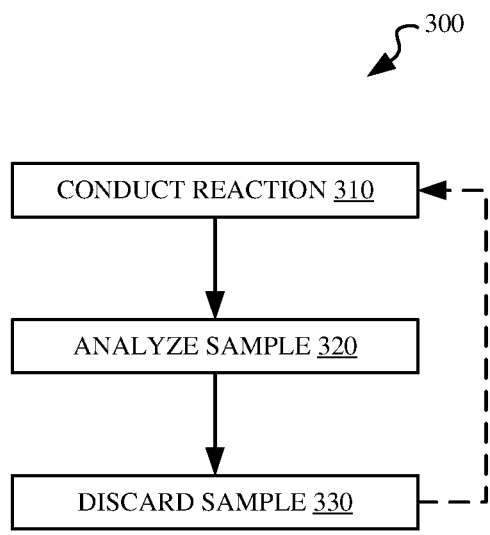
FIG. 3 illustrates an exemplary method of operating a wet chemistry analyzer in accordance with one embodiment of the present invention.

FIG. 3 illustrates an exemplary method of operating a wet chemistry analyzer in accordance with one embodiment of the present invention. Method 300 illustrates one example of a normal operating procedure for a wet chemistry analyzer, for example wet chemistry analyzer 200, shown in FIG. 2.

In block 310, a reaction is conducted within a reaction chamber of a wet chemistry analyzer, in one embodiment. The reaction may comprise, for example a molybdenum blue reaction, configured to render silica within a sample detectable by colorimetric analysis. The reaction can be characterized by a reaction time, which may comprise the time it takes to reach equilibrium, or completion. In block 310, the reaction may be conducted, for example by providing reactants, for example reactants 232, and/or solvents, for example solvents 234 from a reagent store, for example reagent store 230, to a reaction chamber, for example chamber 210. The reaction may also comprise adding in a mixing agent, which may comprise a mechanical mixing agent such as stirring, or a chemical mixing agent, for example compressed air.

In block 320, a sample of a completed reaction is analyzed. This may comprise, in one embodiment, providing a sample of the completed reaction from a reaction chamber to an analysis chamber. In one embodiment, the analysis chamber utilizes colorimetric analysis to detect a concentration of an expected reactant or product within the provided sample. The output of the analysis may, for example, be provided to an operator of a wet chemistry analyzer. The output may be provided, in one embodiment, by a visual indication on a display external to the wet chemistry analyzer. In another embodiment, the output is provided by sending an indication wirelessly to an operator, for example, as a text message or transmitted and displayed on an external display associated with another computing device. In at least one embodiment, after a sample is analyzed, it is discarded, as illustrated in block 330.

Figure 4:
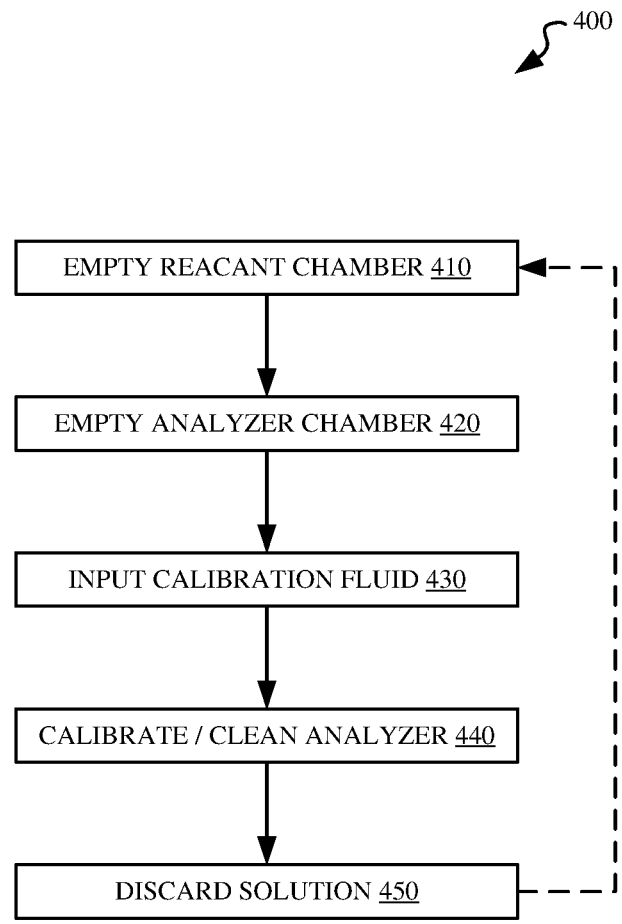
FIG. 4 illustrates an exemplary method of calibrating and cleaning a wet chemistry analyzer in accordance with one embodiment of the present invention.

FIG. 4 illustrates an exemplary method of calibrating and cleaning a wet chemistry analyzer in accordance with one embodiment of the present invention. In one embodiment, an analyzer can either complete method 300 or method 400, but not both at the same time. Selection of either method 300 or method 400 may be made, in one embodiment, on an automated schedule, for example after a predetermined time period or a predetermined number of cycles through method 300. In another embodiment, selection of either method 300 or method 400 is controlled by a user of an analyzer, for example through an input mechanism such as input 104, or input 202.

For example, in one embodiment, method 300 repeats a number of times before a wet chemistry analyzer requires cleaning and/or calibration. However, after a certain number of analyses are completed, a wet chemistry analyzer should be calibrated in order to ensure accuracy. Similarly, at the same number of cycles, or after a different number of cycles, the analyzer should also be cleaned in order to remove excess precipitant build-up within the machine. Method 400 illustrates one example method for calibrating and cleaning a wet chemistry analyzer in accordance with one embodiment.

In block 410, a reactant chamber is emptied. This may comprise, for example, removal of leftover materials from a previous reaction cycle, for example a cycle through method 300, for example by transfer to a waste stream. In another embodiment, the reactant chamber is simultaneously emptied as another fluid moves into the chamber, for example air moving through a valve assembly of an analyzer such that it displaces a reaction mixture. In another embodiment, the reactant chamber is simultaneously emptied as a cleaning and/or calibration fluid is pumped into the chamber such that the cleaning fluid displaces the reaction mixture as a cleaning cycle begins.

In block 420, an analysis chamber is emptied, for example after an analysis has been completed. This may comprise moving a previously analyzed sample from the analysis chamber to a waste storage chamber. In another embodiment, the analysis chamber is simultaneously emptied as another fluid moves into the chamber, for example air moving through a valve assembly of an analyzer such that it displaces a sample. In another embodiment, the analysis chamber is simultaneously emptied as a cleaning and/or calibration fluid is pumped into the chamber such that the cleaning fluid displaces the sample as a cleaning cycle begins.

In block 430, a calibration solution is introduced to the wet chemistry analyzer. For example, in one embodiment, the calibration fluid flows through a reaction chamber and an analysis chamber such that it passes through all chambers and piping occupied by reagent fluids during a cycle through method 300. In one embodiment, the reactant and/or analyzer chamber do not need to be emptied before the calibration fluid is introduced. For example, a pump and valve configuration may simultaneously remove reactant and analyzer fluids as they feed calibration fluid into the analyzer, such that, for example, the calibration fluid pushes out any remaining fluid in the reactant chamber or analysis chamber.

In one embodiment, the calibration fluid used in block 430 comprises a cleaning agent. The cleaning agent can be selected based on the most likely precipitates expected within the wet chemistry analyzer. For example, if the wet chemistry analyzer periodically conducts reactions with acidic reactants or products, a strong base may be desired in order to dissolve acidic precipitants. In another embodiment, where the wet chemistry analyzer conducts experiments with bases as reactants or products, a strong acid may be required in order to remove basic precipitants.

In one embodiment, for example where the analyzer conducts a molybdenum blue reaction, the cleaning agent comprises sodium hydroxide or another exemplary strong base configured to react with silicamolybdic acid precipitates that may build up within the analyzer. In one embodiment, the sodium hydroxide comprises a percentage by weight of the cleaning solution, for example at least 0.01% by weight. In one embodiment, the sodium hydroxide comprises at least 0.02% by weight of the cleaning solution. In another embodiment, the sodium hydroxide comprises at least 0.15%, or at least 0.2%, or an even greater percentage of the cleaning solution. However, it is important to note that strong acids and strong bases, in high concentrations, may corrode internal components of a wet chemistry analyzer. Therefore, it may be advantageous to use a lower concentration of acid or base within the wet chemistry analyzer, but allow for a longer cleaning period, or the use of a greater volume of calibration fluid in order to ensure that all precipitants dissolve.

In block 440, the wet chemistry analyzer is simultaneously calibrated and cleaned by exposure to the calibration solution and cleaning agent. In one embodiment, the calibration fluid is used to conduct a calibration cycle of the wet chemistry analyzer, which may comprise any known calibration method. For example, the calibration fluid with cleaning agent may have a known absorbance or transmissivity such that an accuracy of the analyzer can be compared to known parameters of the calibration fluid. While the calibration occurs, the cleaning agent within the calibration solution may function as an agent to dissolve any precipitant build-up within any part of the wet chemistry analyzer, without interfering with the accuracy of the calibration method selected.

In block 450, used calibration solution is discarded. For example, after a calibration and cleaning operation has been completed, the used solution is provided to a waste stream. In one embodiment, the solution is analyzed in order to determine whether cleaning is complete, or if method 400 should repeat. For example, a pH of the solution may be tested as, for example, a basic cleaning solution will have a lower pH after interacting with acidic deposits. Conversely, an acidic cleaning solution will have a higher pH after interacting with basic deposits. Discarding the leftover calibration solution may also comprise repeating method 400 a number of times in order to ensure that the wet chemistry analyzer is sufficiently calibrated and cleaned, such that used calibration fluid is discarded after each cycle. Alternatively, the same calibration solution may be recycled through the analyzer as method 400 is repeated. Discarding the sample may also comprise running an inert fluid through the system after the calibration cycle is compete, in order to ensure that all calibration and cleaning agents are fully removed from the system. For example in a wet chemistry analyzer that conducts primarily water-based reactions, water may be used as an inert fluid to push out, or remove any leftover calibration or cleaning solution.

Although the present invention has been described with reference to preferred embodiments, workers skilled in the art will recognize that changes may be made in form and detail without departing from the spirit and scope of the invention.

What is claimed is:

1. A calibration solution for a wet chemistry analyzer, the calibration solution comprising:
   a calibration agent;
   a cleaning agent comprising a strong base; and
   wherein the cleaning agent is selected such that the wet chemistry analyzer is simultaneously cleaned and calibrated.

2. The solution of claim 1, wherein the cleaning agent is selected at least in part based on a reagent used in the wet chemistry analyzer.

3. The solution of claim 1, wherein the cleaning agent comprises sodium hydroxide.

4. The solution of claim 3, wherein the cleaning agent comprises at least 0.01% by weight sodium hydroxide.

5. A wet chemistry analyzer comprising:
   a reaction chamber configured to house a reaction mixture and configured to conduct a reaction with a reagent within the reaction mixture;
   a detector configured to detect a process variable indicative of the reaction mixture;
   a reagent housing configured to house a calibration fluid; and
   wherein the calibration fluid comprises a calibration agent and a cleaning agent, and wherein the calibration fluid is configured to simultaneously clean and calibrate the wet chemistry analyzer during a calibration cycle.

6. The analyzer of claim 5, wherein the calibration fluid comprises a cleaning agent.

7. The analyzer of claim 6, wherein the cleaning agent is selected to react with a component of the reaction mixture.

8. The analyzer of claim 6, wherein the cleaning agent comprises a strong base.

9. The analyzer of claim 6, wherein the cleaning agent comprises a strong acid.

10. The analyzer of claim 5, wherein the calibration cycle comprises providing the calibration fluid through the analyzer such that it fluidically contacts a surface configured to receive the reaction mixture.

* * * * *